United States Patent [19]
Sandberg et al.

[11] Patent Number: 6,069,129
[45] Date of Patent: May 30, 2000

[54] ELASTIN DERIVED COMPOSITION AND METHOD OF USING SAME

[75] Inventors: Lawrence B. Sandberg, Colton; Philip J. Roos, Loma Linda; Thomas F. Mitts, Visalia, all of Calif.

[73] Assignee: MRS, LLC, Visalia, Calif.

[21] Appl. No.: 09/039,308

[22] Filed: Mar. 13, 1998

[51] Int. Cl.$^7$ .......................... A61K 38/01; A61K 38/08
[52] U.S. Cl. ................... 514/16; 514/17; 514/21; 530/329; 530/330; 435/68.1
[58] Field of Search ...................... 514/16–18; 435/68.1; 530/353

[56] References Cited

U.S. PATENT DOCUMENTS

| | | | |
|---|---|---|---|
| 4,327,078 | 4/1982 | Charlet et al. | 424/45 |
| 4,474,763 | 10/1984 | Lubowe | 424/177 |
| 4,591,501 | 5/1986 | Cioca | 424/28 |
| 4,659,740 | 4/1987 | Usher | 514/773 |
| 4,963,656 | 10/1990 | Mitani | 530/353 |
| 5,017,691 | 5/1991 | Lee | 530/351 |
| 5,079,003 | 1/1992 | Scaffidi et al. | 424/401 |
| 5,223,420 | 6/1993 | Rabaud et al. | 424/425 |
| 5,523,291 | 6/1996 | Janzen et al. | 514/21 |
| 5,648,209 | 7/1997 | Avrameas et al. | 435/5 |

FOREIGN PATENT DOCUMENTS

| | | |
|---|---|---|
| 08225594 | 9/1993 | European Pat. Off. . |

OTHER PUBLICATIONS

Hieber, A. D. et al. Detection of Elastin in the Human Fetal Membranes: Proposed Molecular Basis for Elasticity; Placenta; vol. 18; pp. 301–312; 1997.

Gibson, M. A. et al. Further Characterization of Proteins Associated with Elastic Fiber Microfibrils Including the Molecular Cloning of MAGP–2 (*MP25*); The Journal of Biological Chemistry; vol. 271, No. 2. pp. 1096–1103; Jan. 12, 1996.

Price, L. S. C. et al. Valyl–Alanyl–Prolyl–Glycine (VAPG) Serves as a Quantatative Marker for Human Elastins; Matrix; vol. 13. pp. 307–311; 1993.

Blankenship, J. W. et al. Oxysterol Incorporation Into Rat Aorta Resulting in Elastin Compositional Changes; Lipids; vol. 26, No. 5; pp. 381–384; 1991.

Sandberg, L. B. et al. Quantitation of Elastin in Tissues and Culture: Problems Related to the Accurate Measurement of Small Amounts of Elastin With Special Emphasis on the Rat; Connective Tissue Research; vol. 25, pp. 139–148; 1990.

Sandberg, L. et al. Structural Guidelines for an Acceptable Elastin and Tropoelastin: Application Towards Quantitation of Elastin Accumulation in Tissue Culture; Elastin: Chemical and Biological Aspects (Reprinted); pp. 24–44; 1990.

Sandberg, L. B. et al. Quantitation of Elastin Through Measurement of Its Pentapeptide Content; Biochemical and Biophysical Research Communications; vol. 136, No. 2. pp. 672–678; Apr. 29, 1986.

Database CaPlus, AN 108:167920. Bayer et al. Z. Naturforsch., C: Biosci, 42(4), 455–60), Apr. 1987.

Hunninghake et al. Science, 212, 925–927, May 1981.

Database Caplus, DN 127:219499. Morrelli et al. J. Pept. Res., 49 (6), 429–499, Jun. 1997.

Database Caplus, DN 122:102414. Bisaccia et al. Int, J. Pept. Res, 44, 332–341, Apr. 1994.

*Primary Examiner*—Michael P. Woodward
*Assistant Examiner*—Michael Borin
*Attorney, Agent, or Firm*—Reed Smith Shaw & McClay, LLP; Raymond A. Miller

[57] ABSTRACT

The present invention is directed to a formulation or composition which is used to enhance the softness, elastin, or appearance of tissue by increasing the endogenous elastin production. Specifically, the present invention is directed to a composition formulated from the products of thermolysin digestion which are filtered through a 10,000 molecular weight cutoff device, which may be dried to have a formulation which contains 90% or greater of peptides having a molecular weight lower than 10,000 Da. This formulation is preferably applied to human skin in a cosmetic or therapeutic formulation and results in enhanced elasticity of the skin.

46 Claims, 3 Drawing Sheets

ELASTIN DERIVED COMPOSITION AND METHOD OF USING SAME

BACKGROUND OF THE INVENTION

1. Field of the Invention

This invention relates generally to a composition useful in treating tissue and a method for treating tissue, wherein the composition utilized to treat the tissue includes a peptide which simulates the effect of elastin, and more preferably increases the native production of elastin. Preferably the peptide has an amino acid sequence which corresponds to or is homologous with a fragment of mammalian elastin, more preferably the amino acid sequence corresponds or is homologous with fragments of elastin endogenous to the tissue being treated. It is preferable that the peptide is at a therapeutically effective concentration and/or is an active ingredient of a therapeutic or cosmetic composition. More specifically, the present invention relates to a composition which includes a peptide or multiple peptides which increase the elasticity and turgor of the skin. The present invention is also directed to a method of administering the composition to a patient in need thereof to thereby increase the elasticity of the patient's skin. Increased elasticity results in an improvement in the overall physical appearance of the skin. For example, when treated with the present invention, mammalian skin appears to be softer, smoother, healthier, and more youthful.

2. Background and Description of the Related Art

Skin, in particular mammalian skin consists of a number of overlapping layers of cells. The outermost layer of mammalian skin is called the stratum corneum. This layer protects mammalian skin from physical and atmospheric harm, acting as a barrier to external dangers. The degree of softness or texture of the stratum corneum is directly dependent on its moisture content However, it has been found that, in the lower layers of the skin, degenerative changes which occur with age are not caused principally by a lack of moisture. Therefore, even though the texture and appearance of the skin is dependent on the moisture content of the skin, other factors have been shown to influence the overall appearance and texture of the skin. For example, it has been found that the loss of elasticity in the skin decreases the tone and turgor of the skin. It is speculated that the decrease in skin tone and turgor occurs through degradation of certain complex polypeptides which are present in the skin. These complex polypeptides include elastin and collagen, among others.

Elastin is a highly cross-linked complex polypeptide and is a major component of elastic fibers present in the skin and connective tissue of animals. Elastin appears to be primarily responsible for the physiological elasticity of tissue. In normal mammalian skin, specifically human skin, elastic tissue proteins represent a relatively small fraction of the total dermal proteins, but play a very important role in maintaining or improving the skin tone and structure. Elastin itself is the main protein substance present in elastic fibers and occurs in tendons, blood vessels, and connective tissue. When isolated from these sources, it is normally in the form of a brittle. fibrous, yellowish material which is insoluble in water, alcohol and ether but is somewhat soluble in concentrated aqueous alkali metal hydroxide solutions. The dense cross-linked structure of elastin makes it very difficult to solubilize. There have been many attempts to solubilize elastin and create cosmetic agents from the solubilized elastin. To date, these techniques have not found a large degree of commercial success. Attempts to solubilize are described for example in a U.S. Pat. No. 4,327,078. However, it has been found that elastin is only slightly absorbed by the skin and does not sufficiently penetrate the skin to produce substantial benefits to the skin.

SUMMARY OF THE PRESENT INVENTION

The present invention is directed to a composition which is either therapeutic, cosmetic or both to the tissue to which it is applied. The composition of the present invention preferably modifies or appears to modify the physical characteristics of the tissue to which it is applied, and the tissue being modified is preferably mammalian skin tissue. The composition generally includes a vehicle or carrier for therapeutic or cosmetic administration in which the peptides are formulated at therapeutically effective concentrations to increase the elasticity of the skin. The peptides are preferably soluble in an aqueous solution, and more preferably are comprised of small peptides (usually less than about 10 amino acids in length). It is preferable that the peptide portion of the composition be comprised of peptides having molecular weights of less than 10,000 Da, even more preferably comprised of about 90% of peptides having a molecular weight of less than 10,000 Da. Even more preferably the peptide content of the composition is comprised of peptides having a molecular weight of less than about 3,000 Da, even more preferably the peptide content of the composition is comprised of peptides having a molecular weight of less than about 1,000 Da. In fact, it has been found that the preferred molecular weight range of peptides utilized in the present invention is in the range of about 100–1,000 Da; more preferred about 150–800 Da; even more preferred about 180–600 Da; and most preferably the therapeutic or cosmetic composition includes peptides having a molecular weight in the range of about 188–585 Da.

It has also been found that the peptides which best accomplish an increase in tissue elasticity and turgor are ones which correspond to or are homologous with portions of elastin, particularly with peptides which correspond to or are homologous with portions of elastin endogenous to the tissue being treated. Accordingly, it has been found that digestion of elastin, for example hydrolytic or site specific enzymatic cleavage of the elastin results in peptides which are particularly suitable for use in the present invention. Accordingly, the peptides which result from digesting can be used directly in the therapeutic formulation of the present invention or may be analyzed and sequenced and synthesized by those methods known in the art (i.e. solid state, liquid, and over expression). As used herein, the term "peptide" is not meant to convey any meaning regarding the precursor material or methods utilized to synthesize or make the peptides. Additionally, the term "elastin peptide fragment" in either singular or plural form refers to the fact that the peptide or amino acid sequence being discussed corresponds to, is the biological equivalent of, or is homologous with, a portion of elastin, more specifically to a portion or fragment of elastin endogenous to the animal being treated. However, the term "elastin peptide fragment" is not meant to convey any meaning regarding the source or starting material or method of use to make the elastin peptide fragment. As stated above, peptides of the present invention are preferably formed by enzymatic cleavage of elastin and are even more preferably formed by cleavage of elastin with thermolysin to form hydrophilic elastin derived peptides. It is also preferable that the peptides of the present invention are at a therapeutically effective concentration within the therapeutic or cosmetic composition, wherein the therapeutically effective concentration is in a range of about 0.0002% to about 90% by weight of peptide, more preferably in a range of about 0.05% to about 50% peptide, even more preferably in a range of about 0.5% to about 10% peptide, even more preferably about 1.5% peptide, and most preferably about 1.3% hydrolyzed elastin peptide. The therapeutic composition of the present invention can be formulated as a cosmetic preparation to be applied topically to a patient's skin, such as in an emulsion, lotion, spray, powder, ointment, cream, or foam or in other suitable pharmaceutical vehicles or carriers commonly known in the art for other types of administration (i.e., subcutaneous). The delivery system of the present invention is preferably a topical delivery system but also may be a subcutaneous, transcutaneous, oral, nasal, aerosol, or patch delivery system.

The present invention is further directed to a composition for improving tissue texture, wherein the composition is comprised of an elastin peptide which is synthesized by selectively cleaving elastin. Preferably the composition includes a pharmaceutical delivery system and the elastin is derived from animal tissue. More preferably, *ligamentum nuchea* is the source of the elastin starting material used in the present invention. The elastin of the present invention is preferably selectively cleaved by enzymatic digestion of the elastin with thermolysin. This thermolytic cleavage preferably results in a elastin peptide fragment or fragments having a molecular weight of less than about 10,000 Da, more preferably less than about 3,000 Da, even more preferably less than about 1,000 Da. A preferred composition of the present invention is one in which the elastin peptide fragment or fragments have a molecular weight of less than 1.000 Da. It is also preferable that the elastin peptides fragment or fragments include a sequence according to the formula of $R_1$-Prolyl-Glycine-$R_2$, wherein $R_1$ is an amino acid or amino acid sequence (peptide) which is at the amino terminal and $R_2$ is an amino acid or amino acid sequence (peptide) which is at the carboxyl terminal.

The present invention is further directed to a method of enhancing the functionality, tone, turgor, and elasticity of the tissue to which it is administered which entails administrating effective amounts of an elastin peptide fragment to the tissue. With particularity to skin tissue, the appearance of the skin is enhanced as a consequence of improving the elasticity of the tissue to which the elastin peptide fragment is applied. It is most preferable that the method include the step of stimulating endogenous production of elastin in the patient to which the elastin fragment peptide is being applied. It is preferable that the administration step be comprised of a number of separate administration steps which are repeated most preferably twice daily over a predetermined time, wherein the predetermined time exceeds one week of daily administration of the elastin peptide fragment, more preferably two weeks, and most preferably at least a month of daily topical application (with twice daily of the elastin peptide fragment administration over the month being even more preferable.). As with the composition of the present invention, in the method of the present invention, it is preferable that the composition utilized include an elastin peptide fragment comprised of peptides having a molecular weight of less than about 10,000 Da, more preferably 90% of the peptides have a molecular weight of less than about 10,000 Da It is even more preferable that the elastin peptide fragment be comprised of peptides having a molecular weight of less than about 3,000 Da and most preferably less than about 1,000 Da In one embodiment of the present invention, it is preferable that the elastin peptide fragment or fragments be formed by enzymatic cleavage of the elastin and that the elastin is derived from animal tissue. It is preferable that the enzymatic cleavage occurs via enzymatic treatment of purified elastin starting material with thermolysin.

BRIEF DESCRIPTION OF THE DRAWINGS

The features, aspects, and advantages of the present invention will become better understood with regard to the following description, appended claims, and accompanying drawings where:

DETAILED DESCRIPTION OF THE PREFERRED EMBODIMENT

Figure 1:
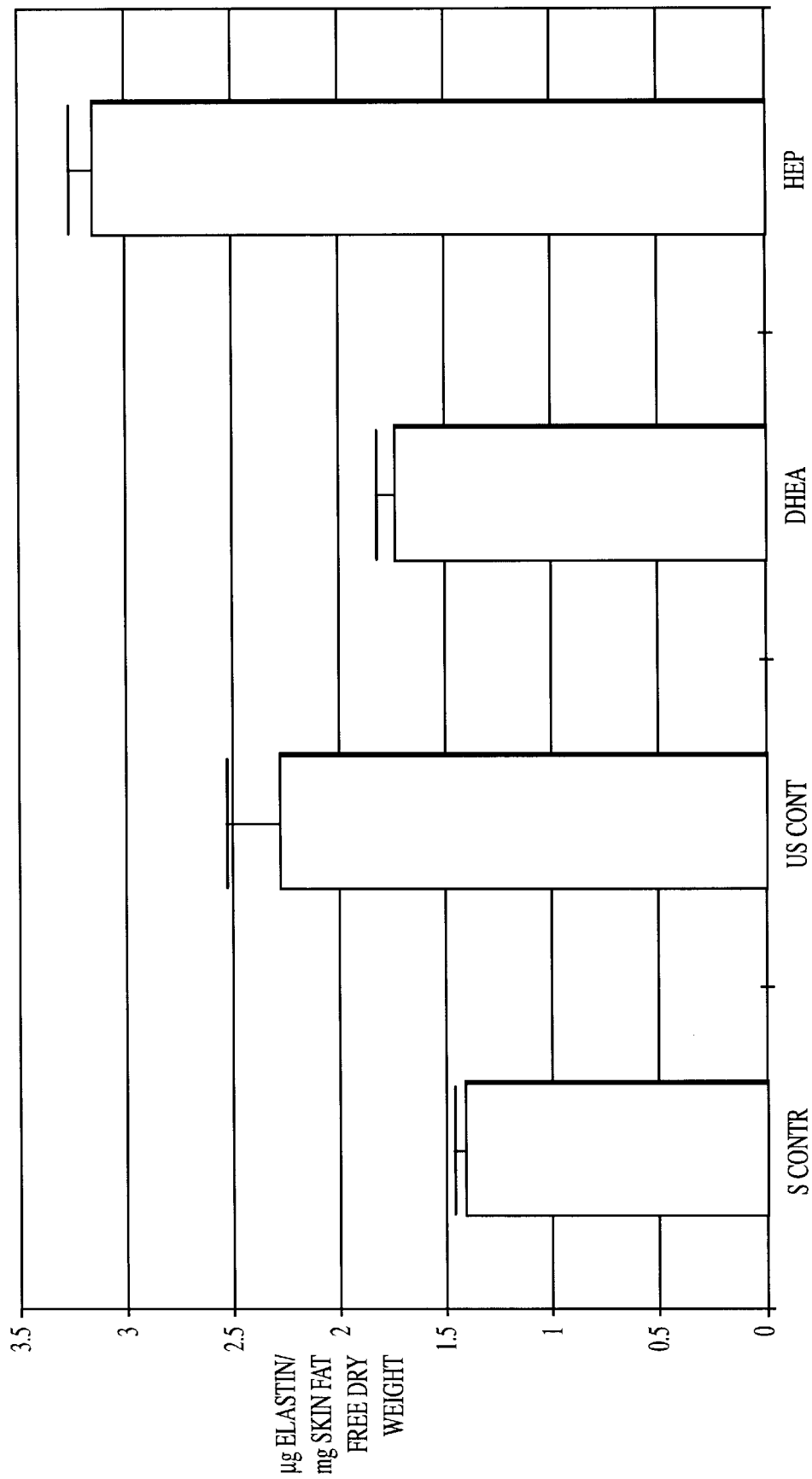
FIG. 1 is a bar graph illustrating increased elastin production as a result of application of the present invention to mammalian skin.
Figure 2A:
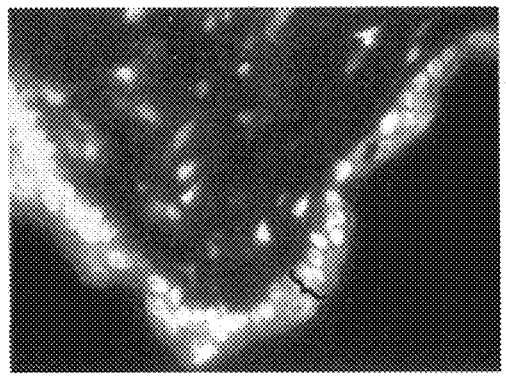
FIG. 2 is a micrograph illustrating the microvascular response of the skin tissue with the present invention.
Figure 2B:
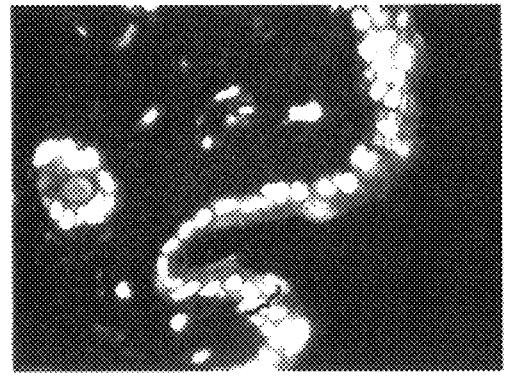
Figure 2C:
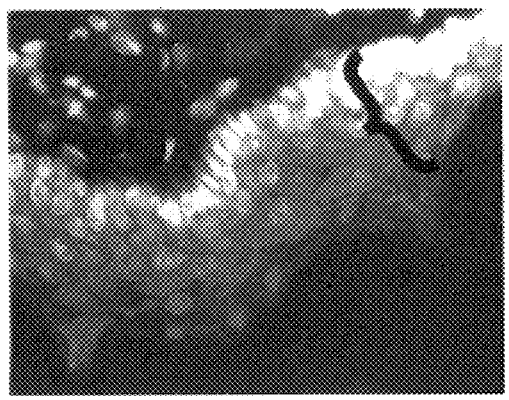
Figure 2D:
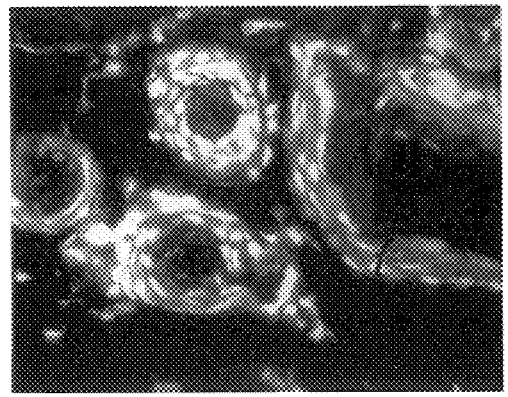

In order that the invention herein described may be more fully understood, the following detailed description is set forth. The present invention relates to composition which is useful in increasing the elasticity of tissue. The present invention is also directed to administering therapeutically effective concentrations of the composition to the tissue in need thereof.

As used herein, the term "subject" or "patient" means any mammal, including humans, in which elastin is utilized for proper tissue function. The methods herein for use contemplate prophylactic use as well as curative use in therapy of an existing condition.

As used herein, the term "abouf" means plus or minus 10% of the numerical value of the number with which it is being used. Therefore, about 50% means in the range of 45%–55%. As used herein, the term "Dalton" (or "Da") refers to the unit of mass which is equivalent to the mass of a hydrogen atom ($1.66 \times 10^{-24}$ gram). Generally speaking, the term "tissue" refers to any aggregation of similarly specialized cells which are united in the performance of a particular function. As used herein, "tissue", unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity. Unless otherwise indicated, the term "skin" means that outer integument or covering of the body, consisting of the dermis and the epidermis and resting upon subcutaneous tissue.

"Providing" when used in conjunction with a therapeutic means to administer a therapeutic directly into or onto a target tissue or to administer a therapeutic to a patient whereby the therapeutic positively impacts the tissue to which it is targeted. Thus, as used herein, the term "providing", when used in conjunction with elastin peptide fragment, can include, but is not limited to, providing an elastin peptide fragment into or onto the target tissue; providing an elastin peptide fragment systemically to a patient by, e.g., intravenous injection whereby the therapeutic reaches the target tissue; providing an elastin peptide fragment in the form of the encoding sequence thereof to the target tissue (e.g., by so-called gene-therapy techniques) whereby the elastin peptide fragment is expressed within the target tissue.

Details on techniques for formulation and administration of pharmaceuticals may be found in the latest edition of Remington's Pharmaceutical Sciences (Mack Publishing Co, Easton Pa.). Although local topical delivery is desirable, there are other means of delivery, for example: oral, parenteral, aerosol, intramuscular, subcutaneous, transcutaneous, intamedullary, intrathecal, intraventricular, intravenous, intraperitoneal, or intranasal administration.

As used herein, the term "therapeutic" means an agent utilized to treat, combat, ameliorate, prevent or improve an unwanted condition or disease of a patient. The condition being treated in the present invention is deficient elastin in tissue, that is, a need in the tissue for more elastin. As it applies to skin, it is measured by turgor, tone, appearance, degree of wrinkles, and youthfulness. As the term applies to blood vessels it may be measured by the degree of elasticity or proper vasomotor response (vasodilatation/vasoconstriction) of the vessel. Accordingly, therapeutic treatment of blood vessels may have implications in diseases associated with visco-elasticity, including hypertension, arteriosclerosis, angina, angiogenesis, myocardial infarction, coronary thrombosis, restenosis post angioplasty, and chronic obstructive pulmonary disease.

Finally, the term "cosmetic," as used herein, refers to a beautifying substance or preparation which preserves, restores, bestows, simulates, or enhances the appearance of bodily beauty, specifically as it relates to the appearance of tissue or skin.

As stated above, the present invention is directed to an elastin peptide fragment which is useful as a therapeutic and or cosmetic composition or agent for modifying tissue, especially skin. The term "modify" is used to convey that the present invention changes either the appearance, form, characteristics and/or the physical attributes of the tissue to which it is being provided, applied or administered. The change in form can be reflected in any of the following alone or in combination: enhanced appearance of the skin; increased softness of the skin; increased turgor of the skin; increased texture of the skin; increased elasticity of the skin; decreased wrinkle formation and increased endogenous elastin production in the skin.

The source of the starting elastin material can derive from a number of sources known in the art. It is known, for example, that the *ligamentum nuchae* is made up largely of elastin, with only a relatively small amount of collagen. More than 70% of the dry weight of this ligament is elastin. Due to the relatively high elastin content and relatively low collagen content of *ligamentum nuchae*, it is an ideal starting material to use in deriving the elastin peptide fragments of the present invention. In a preferred embodiment of the present invention, *ligamentum nuchae* is utilized. It may be preferable to clean the *ligamentum nuchae* first using a procedure similar to that disclosed in U.S. Pat. No. 5,028,695, which this portion of is incorporated herein by reference hereto. Although the preferred source of the starting material of the present invention is *ligamentum nuchae*, other ligaments, tendons, connective tissue, tissue. and synthetic sources may also be used. For example, the arteries and lungs, and other animal tissue, especially those which have significant amounts of elastin, can be used. Also, elastin from different sources, or elastin and collagen from the same or different sources could be mixed together to produce a particular advantageous mix suitable for an intended use. For example, rat, sheep, and porcine aorta can be used as a source of elastin as described in L. B. Sandberg, *Connective Tissue Research*, 1990, Vol. 25, pp. 139–148. which is hereby incorporated herein in its entirety by reference hereto.

In the present invention, the ligament extraction is comprised of taking dissected *ligamentum nuchae* ligaments and removing as much fat and excess connective tissue as possible. These "clean" ligaments are then chopped into about one centimeter square (1 cm$^2$) pieces and washed with doubly distilled water ("DDW"). The clean ligaments are then placed on a metal mortar, pre-chilled to −20° F. and liquid nitrogen is added to freeze the tissue. The ligaments are then minced or pulverized with the appropriate tool and re-suspended in 1% aqueous NaCl at a ratio of about 100 grams of tissue to about three liters of 1% aqueous NaCl and homogenized in a Waring blender at high speed for 30–60 seconds. The homogenized ligament is transferred to a four-liter beaker and stirred overnight at 4° C. on a magnetic stirrer, after which it is centrifuged at 32,500×G and the supernatant is checked for protein content using the Biuret method for protein determination. The Biuret reaction is done by mixing 2 milliliters of extract with 3 milliliters of reagent and reading immediately either by simple visual inspection or at 540 nanometers on a spectrophotometer to determine the protein concentration of the supernatant. The supernatant is then discarded. The pellet (referred to hereinafter as the elastin pellet) is resuspended in 1% aqueous NaCl and homogenized. The process of homogenizing in a Waring blender, stirring overnight and centrifuging are repeated three to four times until the supernatant is Biuret negative. After centrifugation, the elastin pellet is resuspended in DDW and autoclaved 30 psi for six hours. The resuspended elastin pellet is centrifuged again and the supernatant is tested for protein content via the Biuret method. The elastin is washed with boiling DDW and then with DDW at room temperature and the washes are tested for protein content via the Biuret method. If the washes are Biuret negative, the elastin pellet is dried with chloroform/methanol solution at a ratio of 2 parts chloroform to 1 part methanol. If the Biuret test is positive, the six hour autoclave procedure with wash step is repeated until the Biuret test is negative. Finally, the elastin residue is washed with five volumes of pure methanol and air-dried at room temperature. The elastin residue is transferred to a desiccator and dried over $P_2O_5$ for 24 hours until the weight of the elastin residue is stable. The elastin residue is then milled in a Willey mill through a 40-mesh screen followed by a 60-mesh screen.

For the thermolysin digestion, three times re-crystallized thermolysin product from CalBiochem (10394 Pacific Center Court, San Diego, Calif. 92121) is used. The thermolysin preparation contains sufficient calcium to ensure maximal activity of the enzyme. The thermolysin digestion is done as follows: a waterbath is brought to a 55° C. temperature with a rotary shaker and five grams of the finely milled largely insoluble elastin residue is hydrated with one liter of DDW for fifteen minutes at room temperature. After hydration, the one liter DDW which contains the five grams of elastin is placed in the 55° C. bath and the pH of the elastin/water mixture is brought to a pH between 7–8 with 10% methylamine. Fifty milligrams of thermolysin (*bacillus thermoproteolyticus*) is added directly to the elastin water mixture. The thermolysin contains about 60% protein (60.2%), about 13% (13.2%) sodium acetate, and about 25% (25.3%) calcium acetate, with a specific activity of about 8,720 I.U./mg dry weight. The pH of the elastin water mixture is monitored with a pH meter or pH stat and adjusted with 10% methylamine to keep the pH between 6.8 and 7.5. The digestion is allowed to continue for 75 minutes and then concentrated hydrochloric acid is added to adjust the pH to 3.0 to terminate the digestion.

After digestion is terminated, the digested product is filtered through a PM 10 Diaflow 10,000 molecular weight cut-off ultra-filtration membrane to filter out any protein or peptides exceeding about 10,000 Da molecular weight. The resulting supernatant is an elastin-derived composition comprised of peptides having a molecular weight of less than about 10,000 Da. As it turns out, the most preferred composition is comprised of an elastin peptide fragment with a molecular weight of less than about 1,000 Da. Table 1 is a list of peptide sequences isolated from the thermolytic cleavage of elastin. These isolated fractions, either alone or in combination, when applied to tissue, result in the tissue, specifically mammalian skin, exhibiting characteristics of increased skin elasticity, including skin softness and increased turgor as well as an overall increase in the attractiveness of the skin. As can be seen from Table 1 below, it is preferable that the composition of the present invention be comprised of elastin peptide fragments having an amino acid chain length of less than about 10 amino acids or having a molecular weight in the range of about 150–800 Da, even more preferably about 180 Da to about 600 Da, and most preferably from about 188 Da to about 585 Da. It is also preferable that the peptide or peptides used in formulating the composition of the present invention are comprised substantially of amino acids having an apolar and/or an uncharged side group (i.e. alanine, valine, proline, glycine), more preferably comprised of peptides which include glycine or proline, and even more preferably comprised of peptides containing glycine and proline in each amino acid sequence.

The elastin peptide fragments which have been identified as being particularly useful in the present invention have the following amino acid sequences:

TABLE 1

| SEQ # | PEPTIDE | MOL WT | NAME (N- to C-terminal) | c-DNA Copies |
|---|---|---|---|---|
| 1. | AVG | 245 | Alanine-Valine-Glycine | 1 |
| 2. | VGAG | 302 | Valine-Glycine-Alanine-Glycine | 2 |
| 3. | IGG | 302 | Isoleucine-Glycine-Glycine | 4 |
| 4. | LG | 188 | Leucine-Glycine | 26 |
| 5. | IGAG | 316 | Isoleucine-Glycine-Alanine-Glycine | 2 |
| 6. | LGG | 245 | Leucine-Glycine-Glycine | 6 |
| 7. | VAPG | 342 | Valine-Alanine-Proline-Glycine | 2 |
| 8. | LGPG | 342 | Leucine-Glycine-Proline-Glycine | 3 |
| 9. | LGAG | 316 | Leucine-Glycine-Alanine-Glycine | 4 |
| 10. | VGPG | 328 | Valine-Glycine-Proline-Glycine | 2 |
| 11. | FGPG | 376 | Phenylalanine-Glycine-Proline-Glycine | 2 |
| 12. | VGPQ | 399 | Valine-Glycine-Proline-Glutamine | 1 |
| 13. | LGA | 259 | Leucine-Glycine-Alanine | 7 |
| 14. | VGPA | 342 | Valine-Glycine-Proline-Alanine | 1 |
| 15. | VVPG | 370 | Valine-Valine-Proline-Glycine | 2 |
| 16. | AVPG | 342 | Alanine-Valine-Proline-Glycine | 2 |
| 17. | VVPQ | 441 | Valine-Valine-Proline-Glutamine | 1 |
| 18. | VAARPG | 569 | Valine-Alanine-Alanine-Arginine-Proline-Glycine | 1 |
| 19. | LGAGGAG | 501 | Leucine-Glycine-Alanine-Glycine-Glycine-Alanine-Glycine | 1 |
| 20. | AIPG | 356 | Alanine-Isoleucine-Proline-Glycine | 2 |
| 21. | LGPGG | 399 | Leucine-Glycine-Proline-Glycine-Glycine | 1 |
| 22. | AAAQA | 430 | Alanine-Alanine-Alanine-Glutamine-Alanine | 1 |
| 23. | VGVHypG | 444 | Valine-Glycine-Valine-Hydroxyproline-Glycine | 14* |
| 24. | VYPGG | 491 | Valine-Tyrosine-Proline-Glycine-Glycine | 1 |
| 25. | IGGVGG | 458 | Isoleucine-Glycine-Glycine-Valine-Glycine-Glycine | 1 |

TABLE 1-continued

| SEQ # | PEPTIDE | MOL WT | NAME (N- to C-terminal) | c-DNA Copies |
|---|---|---|---|---|
| 26. | VAPGVG | 498 | Valine-Alanine-Proline-Glycine-Valine-Glycine | 1 |
| 27. | LGVGG | 401 | Leucine-Glycine-Valine-Glycine-Glycine | 3 |
| 28. | VLPG | 384 | Valine-Luecine-Proline-Glycine | 3 |
| 29. | FRAAA | 534 | Phenylalanine-Arginine-Alanine-Alanine-Alanine | 1 |
| 30. | VGGVPG | 484 | Valine-Glycine-Glycine-Valine-Proline-Glycine | 1 |
| 31. | FGPGG | 433 | Phenylalanine-Glycine-Proline-Glycine-Glycine | 1 |
| 32. | VGVPG | 427 | Valine-Glycine-Valine-Proline-Glycine | 14* |
| 33. | VLPGAG | 512 | Valine-Leucine-Proline-Glycine-Alanine-Glycine | 1 |
| 34. | VGLHypG | 458 | Valine-Glycine-Leucine-Hydroxyproline-Glycine | 1** |
| 35. | LGVGA | 415 | Leucine-Glycine-Valine-Glycine-Alanine | 1 |
| 36. | AFPG | 390 | Alanine-Phenylalanine-Proline-Glycine | 1 |
| 37. | AFPGA | 461 | Alanine-Phenylalanine-Proline-Glycine-Alanine | 1 |
| 38. | VGIPA | 455 | Valine-Glycine-Isoleucine-Proline-Alanine | 1 |
| 39. | VGGIPT | 542 | Valine-Glycine-Glycine-Isoleucine-Proline-Threonine | no |
| 40. | VGVGVPG | 583 | Valine-Glycine-Valine-Glycine-Valine-Proline-Glycine | 2 |
| 41. | LGPGVG | 498 | Leucine-Glycine-Proline-Glycine-Valine-Glycine | 1 |

*Sequence Nos. 23 and 32 appear to be a common sequence because Proline hydroxylation is a post-translational event.
**as VGLPG.

It should be noted that the above sequences account for about 40% of all the elastin sequences with the rest of the sequences being reduced to free amino acids or desmosine crosslinks and that these amino acids are not being accounted for with sequencing.

The elastin peptide fragment/water mixture which is obtained upon digestion with thermolysin described is preferably flash evaporated to dryness and redissolved in a small volume of DDW and if desired is diluted sufficiently with DDW for lyophilization to dryness. In the alternative, rather than redissolving the hydrophilic elastin peptide, the filtered product is freeze dried twice, resulting in a powder which contains 30 weight chemically-bound water and very little salt (NaCl). Preferably the powder for therapeutic use is dissolved to a concentration of about 0.0002% to about 90% by weight of elastin peptide fragment, more preferably in a range of about 0.05% to about 50%, even more preferably in a range of about 0.05% to about 10% elastin peptide fragment, and more preferably about 1.5% elastin peptide fragment, and most preferably about 1.3% peptide fragment or fragments in a vehicle which is suitable for topical or subcutaneous administration.

As can be seen from FIG. 1, the topical treatment with a composition which included peptide fragments at a concentration of about 1.3% when applied to the skin of a Sprague-Dawley male rat over a one month period illustrates a doubling of the elastin content of the skin, as compared to both control samples and similar applications and concentration of DHEA. In FIG. 1, S CONTR represents the Shaven Control and US CONTR represents the Unshaven Control. FIG. 1 illustrates that the present invention has the advantageous qualities of enhancing the softness or elasticity of the skin by increasing the endogenous production of elastin in the skin. The present invention is also directed to a method of improving the texture of skin, specifically the physical appearance of the skin by improving the endogenous production of elastin. The method of the present invention employs any of a number of known administrative routes such as oral, IV, subcutaneous, transcutaneous, and topical administration. The method of the present invention employs a pharmaceutical or cosmetic composition which enhances the physical appearance of and/or the elasticity of tissue due to increased production of endogenous elastin in the tissue to which the formulation is administered. It is believed that the limit for skin penetration of elastin peptide fragment is a molecular weight of about 20,000 Da Due to the fact that the present invention uses peptides derived from elastin through thermolytic cleavage which have a molecular weight of less than about 10,000 Da, more preferably less than about 3,000 Da, even more preferably less than 1,000 Da, the peptides meeting this criteria present in the composition of the present invention are absorbed by the skin upon application. Beyond the increased absorption due to the relative small size of the active peptides of the present invention, the peptides themselves which preferably correspond to those formed through thermolytic cleavage of elastin with thermolysin, appear to have increased activity in the production of endogenous elastin on a skin to which the administration or the therapeutic composition is applied.

The present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. U.S. Pat. No. 4,327,078, which was referenced earlier, is illustrative of the different types of topical administrations which may be employed to administer a soluble elastin-based derivative. In each of the examples provided, the concentration of the elastin peptide fragment of the present invention would be preferably about 1.5% and the concentration of water would be increased to make up the difference.

It is preferable that the topical administration of the composition of the present invention occur repeatedly over a predetermined time period, preferably in the range of about one week to about one month. In the Sprague-Dawley rats used to generate FIG. 1, the rats were treated topically with a 1.3% concentration of the hydrophilic elastin peptide formulated by the method disclosed herein for a period of 30 days. Testing illustrated that the endogenous elastin (measured by microgram ($\mu$g) Elastin per milligram (mg) Skin Fat Free Dry weight) of each of the rats to which the administration was applied doubled over that of a control sample and to a sample which was treated with a 5% concentration of DHEA over a similar time period. Three animals each were used to generate the data for S CONTR, US CONT, and DHEA and eleven animals were used for HEP. Three skin samples from the treated areas of each animal were taken for study, and the three results from each animal were averaged. The mean of these results were: S CONTR (1.408); US CONTR (2.291); DHEA (1.753); HEP (3.175). The elastin content of the skin was determined by a precise assay for rat elastin developed by Sandberg, et al. ("Quantitation of Elastin in Tissues and Culture: problems related to the accurate measurement of mall amounts of elastin with special emphasis on the rat" *Connective Tissue Research*. 25: 139–48, 1990) the assay portion of which is hereby incorporated herein by reference thereto. The data of FIG. 1 are significant at an alpha level less than 0.001 as determined by analysis of variance. This means there is less than one chance in a thousand that the findings occurred by chance.

This data further supports the use of the cosmetic or pharmaceutical preparation over an extended period preferably in the range of one week to one month, more preferably in the range of seven days to about fourteen days and most preferably about fourteen days of daily administration at about 1.5% concentration of elastin peptide or peptides having a molecular weight lower than about 10,000 Da, more preferably less than 1,000 Da and most preferably in the range of about 180 Da to about 600 Da.

FIG. 2 is a micrograph intended to illustrate the increased appearance, and thus beneficial cosmetic implications of the present invention. As can be seen from FIG. 2, skin treated with an elastin peptide fragment appears to be healthier than untreated skin. This is evidenced under a microscope by an increase in vascular response. In FIG. 2, fixed tissue sections of rat skin were labeled with flourescein conjugated antifibronectin antibodies. Panel a in FIG. 2 is a representative sample from the unshaven control tissue; panel b is a representative sample from the shaven control sample; and panel C is a representative sample of the tissue which received DHEA topical treatment Finally, panel d received treatment with the present invention in a topical treatment in accordance with the samples discussed above with regard to FIG. 1. The dermal layer in the control panels (a and b) is relatively uniform and thin compared to the thickness of both panel C and panel d. For convenience, in each of panels a, b, c, and d, the dermal layer is bracketed. Surprisingly and illustrative of some of the benefits obtained utilizing the present invention, panel d illustrates an increased concentration of capillary venules in the subdermal region. The capillary venules are shown in this figure as brightly stained oval bodies that lie beneath the dermal layer. The increase in the concentration of endothelial cells in the subdermal region indicate an increase in capillary density and therefore illustrate the potential for the present invention to be used for the formation of blood vessels or capillary venules (neovascularization or angiogenesis).

It appears that the elastin peptide fragment of the present invention would preferably include sequences of Leucine-Glycine and/or Valine-Glycine-Valine-Hydroxyproline-Glycine, and/or Valine-Glycine-Valine-Proline-Glycine. It would also appear that sequences which contain Glycine and/or Proline are most preferred, and that a composition which includes either or both of these amino acids in a much larger concentration (relative to other amino acids present) are most preferred. While the foregoing has been set forth in considerable detail, the sequences are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein. For example, the composition can be administered via many alternative drug delivery vehicles known in the art, and the composition may be used to treat tissue which is dependent upon elastin for its utility as opposed to its appearance and the elastin peptides can be derived from digestion of elastin synthesis of the amino acid sequence (either solid state or liquid), and from overexpression in a bacterial system. Accordingly, all such variances should be viewed as being within the scope of the present invention as set forth in the claims below.

What is claimed is:

1. A composition useful in treating mammalian tissue, said composition being comprised of a peptide selected from the group consisting of of SEQ ID NO: 17 (Valine-Valine-Proline-Glutamine), SEQ ID NO: 18 (Valine-Alanine-Alanine-Arginine-Proline-Glycine), SEQ ID NO: 19 (Leucine-Glycine-Alanine-Glycine-Glycine-Alanine-Glycine), and SEQ ID NO: 23 (Valine-Glycine-Valine-Hydroxyproline-Glycine).

2. The composition of claim 1, wherein said peptide is soluble in an aqueous solution.

3. The composition of claim 2, wherein said peptide is at a therapeutically effective concentration.

4. The composition of claim 1, wherein said peptide is formed by digestion of elastin with thermolysin.

5. The composition of claim 3, wherein said therapeutically effective concentration is a range of about 0.0002% to about 90%.

6. The composition of claim 5, wherein said therapeutically effective concentration is in the range of about 0.5% to about 10%.

7. The composition of claim 1, wherein said composition is a cosmetic preparation.

8. The composition of claim 7, wherein said cosmetic preparation is selected from the group consisting of an emulsion, lotion, spray, aerosol, powder, ointment, cream and foam.

9. The composition of claim 1, wherein the tissue being treated is a blood vessel.

10. The composition of claim 1, wherein the composition is used for treating a condition selected from the group consisting of hypertension, coronary heart disease, arteriosclerosis, angina, coronary thrombosis, chronic obstructive pulmonary disease, and restenosis post angioplasty.

11. A composition useful in improving tissue turgor, said composition being comprised of a peptide selected from the group consisting of SEQ ID NO: 17 (Valine-Valine-Proline-Glutamine), SEQ ID NO: 18 (Valine-Alanine-Alanine-Arginine-Proline-Glycine), SEQ ID NO: 19 (Leucine-Glycine-Alanine-Glycine-Glycine-Alanine-Glycine), and SEQ ID NO: 23 (Valine-Glycine-Valine-Hydroxyproline-Glycine).

12. The composition of claim 11, wherein said composition further includes a pharmaceutical delivery system.

13. The composition of claim 11, wherein said peptide is derived from elastin.

14. The composition of claim 13, wherein said peptide is derived from animal tissue.

15. The composition of claim 12, wherein said pharmaceutical delivery system is a topical delivery system.

16. The composition of claim 12, wherein said pharmaceutical delivery system is a subcutaneous delivery system.

17. The composition of claim 15, wherein said topical delivery system is selected from the group consisting of a cosmetic preparation, powder, emulsion, lotion, spray, ointment, aerosol, cream and foam.

18. A method of enhancing tissue elasticity, said method being comprised of administering a therapeutically effective concentration of a peptide selected from the group consisting of SEQ ID NO: 17 (Valine-Valine-Proline-Glutamine), SEQ ID NO: 18 (Valine-Alanine-Alanine-Arginine-Proline-Glycine), SEQ ID NO: 19 (Leucine-Glycine-Alanine-Glycine-Glycine-Alanine-Glycine, and SEQ ID NO: 23 (Valine-Glycine-Valine-Hydroxyproline-Glycine).

19. The method of claim 18, wherein the tissue in which elasticity is enhanced is skin.

20. The method of claim 19, wherein the skin's appearance is enhanced.

21. The method claim 18, further including the step of stimulating endogenous production of elastin.

22. The method of claim 18, wherein the tissue is a blood vessel.

23. The method of claim 18, wherein said tissue is deficient in elastin.

24. The method of claim 23, wherein said tissue is lung tissue.

25. The method of claim 21, wherein the step of administering the peptide is repeated over a predetermined time period.

26. The method of claim 25, wherein the predetermined time period exceeds 14 days of twice daily administration of said peptide.

27. A pharmaceutical composition comprised of a peptide selected from the group consisting of SEQ ID NO: 17 (Valine-Valine-Proline-Glutamine), SEQ ID NO: 18 (Valine-Alanine-Alanine-Arginine-Proline-Glycine), SEQ ID NO: 19 (Leucine-Glycine-Alanine-Glycine-Glycine-Alanine-Glycine) and SEQ ID NO: 23 (Valine-Glycine-Valine-Hydroxyproline-Glycine).

28. The pharmaceutical composition of claim 27, wherein application of said composition to a patient results in neovascularization.

29. The pharmaceutical composition of claim 27, wherein application of said composition to a patient results in angiogenesis.

30. A composition comprised of SEQ ID NO: 17 (Valine-Valine-Proline-Glutamine).

31. A composition comprised of SEQ ID NO: 18 (Valine-Alanine-Alanine-Arginine-Proline-Glycine).

32. A composition comprised of is SEQ ID NO: 23 (Valine-Glycine-Valine-Hydroxyproline-Glycine).

33. A composition comprised of SEQ ID NO: 19 (Leucine-Glycine-Alanine-Glycine-Glycine-Alanine-Glycine).

34. The composition of claim 30, wherein said composition is formulated as a topical preparation.

35. The composition of claim 34, wherein said SEQ ID NO: 17 is at an overall concentration of about 0.5% to about 10% (w/w %) in said composition.

36. The composition of claim 34, wherein said composition is formulated as a preparation selected from the group consisting of a cosmetic preparation, powder, emulsion, lotion, spray, ointment, aerosol, cream and foam.

37. The composition of claim 31, wherein said composition is formulated as a topical preparation.

38. The composition of claim 37, wherein said SEQ ID NO: 18 is at an overall concentration of about 0.5% to about 10% (w/w %) in said composition.

39. The composition of claim 37, wherein said composition is formulated as a preparation selected from the group consisting of a cosmetic preparation, powder, emulsion, lotion, spray, ointment, aerosol, cream and foam.

40. The composition of claim 32, wherein said composition is formulated as a topical preparation.

41. The composition of claim 40, wherein said SEQ ID NO: 23 is at an overall concentration of about 0.5% to about 10% (w/w %) in said composition.

42. The composition of claim 40, wherein said composition is formulated as a preparation selected from the group consisting of a cosmetic preparation, powder, emulsion, lotion, spray, ointment, aerosol, cream and foam.

43. The composition of claim 33, wherein said composition is formulated as a topical preparation.

44. The composition of claim 43, wherein said SEQ ID NO: 19 is at an overall concentration of about 0.5% to about 10% (w/w %) in said composition.

45. The composition of claim 33, wherein said composition is formulated as a preparation selected from the group consisting of a cosmetic preparation, powder, emulsion, lotion, spray, ointment, aerosol, cream and foam.

46. The method of claim 18, wherein said peptide is used for treating a condition selected from the group consisting of hypertension, coronary heart disease, arteriosclerosis, angina, coronary thrombosis, chronic obstructive pulmonary disease, and restenosis post angioplasty.

* * * * *

SEQUENCE LISTING (1) GENERAL INFORMATION:

(iii) NUMBER OF SEQUENCES: 41

(2) INFORMATION FOR SEQ ID NO:1:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ala Val Gly
1

(2) INFORMATION FOR SEQ ID NO:2:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Val Gly Ala Gly
1

(2) INFORMATION FOR SEQ ID NO:3:

(i) SEQUENCE CHARACTERISTICS:
        (A) LENGTH: 3 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ile Gly Gly
1

(2) INFORMATION FOR SEQ ID NO:4:

(i) SEQUENCE CHARACTERISTICS:
        (A) LENGTH: 2 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Leu Gly
1

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION:    SEQ ID NO:5:

Ile Gly Ala Gly
1

(2) INFORMATION FOR SEQ ID NO:6:

(i) SEQUENCE CHARACTERISTICS:
           (A) LENGTH:  3 amino acids
           (B) TYPE:  amino acid
           (C) STRANDEDNESS:  single
           (D) TOPOLOGY:  linear (ii) MOLECULE TYPE:  peptide (xi) SEQUENCE DESCRIPTION:    SEQ ID NO:6:

Leu Gly Gly
1

(2) INFORMATION FOR SEQ ID NO:7:

(i) SEQUENCE CHARACTERISTICS:
           (A) LENGTH:  4 amino acids
           (B) TYPE:  amino acid
           (C) STRANDEDNESS:  single
           (D) TOPOLOGY:  linear (ii) MOLECULE TYPE:  peptide (xi) SEQUENCE DESCRIPTION:    SEQ ID NO:7:

Val Ala Pro Gly
1

(2) INFORMATION FOR SEQ ID NO:8:

(i) SEQUENCE CHARACTERISTICS:
           (A) LENGTH:  4 amino acids
           (B) TYPE:  amino acid
           (C) STRANDEDNESS:  single
           (D) TOPOLOGY:  linear (ii) MOLECULE TYPE:  peptide (xi) SEQUENCE DESCRIPTION:    SEQ ID NO:8:

Leu Gly Pro Gly
1

(2) INFORMATION FOR SEQ ID NO:9:

(i) SEQUENCE CHARACTERISTICS:
           (A) LENGTH:  4 amino acids
           (B) TYPE:  amino acid
           (C) STRANDEDNESS:  single
           (D) TOPOLOGY:  linear (ii) MOLECULE TYPE:  peptide (xi) SEQUENCE DESCRIPTION:    SEQ ID NO:9:

Leu Gly Ala Gly
1

(2) INFORMATION FOR SEQ ID NO:10:

(i) SEQUENCE CHARACTERISTICS:
           (A) LENGTH:  4 amino acids
           (B) TYPE:  amino acid
           (C) STRANDEDNESS:  single
           (D) TOPOLOGY:  linear (ii) MOLECULE TYPE:  peptide (xi) SEQUENCE DESCRIPTION:    SEQ ID NO:10:

Val Gly Pro Gly
1

(2) INFORMATION FOR SEQ ID NO:11:

(i) SEQUENCE CHARACTERISTICS:
            (A) LENGTH:  4 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:11:

Phe Gly Pro Gly
1

(2) INFORMATION FOR SEQ ID NO:12:

(i) SEQUENCE CHARACTERISTICS:
            (A) LENGTH:  4 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:12:

Val Gly Pro Gln
1

(2) INFORMATION FOR SEQ ID NO:13:

(i) SEQUENCE CHARACTERISTICS:
            (A) LENGTH:  3 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:13:

Leu Gly Ala
1

(2) INFORMATION FOR SEQ ID NO:14:

(i) SEQUENCE CHARACTERISTICS:
            (A) LENGTH:  4 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:14:

Val Gly Pro Ala
1

(2) INFORMATION FOR SEQ ID NO:15:

(i) SEQUENCE CHARACTERISTICS:
            (A) LENGTH:  4 amino acids
            (B) TYPE:  amino acid
            (C) STRANDEDNESS:  single
            (D) TOPOLOGY:  linear (ii) MOLECULE TYPE:  peptide

```
        (xi) SEQUENCE DESCRIPTION:     SEQ ID NO:15:

Val Val Pro Gly
1

(2) INFORMATION FOR SEQ ID NO:16:

(i) SEQUENCE CHARACTERISTICS:
           (A) LENGTH:   4 amino acids
           (B) TYPE:     amino acid
           (C) STRANDEDNESS:  single
           (D) TOPOLOGY:  linear (ii) MOLECULE TYPE:  peptide (xi) SEQUENCE DESCRIPTION:     SEQ ID NO:16:

Ala Val Pro Gly
1

(2) INFORMATION FOR SEQ ID NO:17:

(i) SEQUENCE CHARACTERISTICS:
           (A) LENGTH:   4 amino acids
           (B) TYPE:     amino acid
           (C) STRANDEDNESS:  single
           (D) TOPOLOGY:  linear (ii) MOLECULE TYPE:  peptide (xi) SEQUENCE DESCRIPTION:     SEQ ID NO:17:

Val Val Pro Gln
1

(2) INFORMATION FOR SEQ ID NO:18:

(i) SEQUENCE CHARACTERISTICS:
           (A) LENGTH:   6 amino acids
           (B) TYPE:     amino acid
           (C) STRANDEDNESS:  single
           (D) TOPOLOGY:  linear (ii) MOLECULE TYPE:  peptide (xi) SEQUENCE DESCRIPTION:     SEQ ID NO:18:

Val Ala Ala Arg Pro Gly
1               5

(2) INFORMATION FOR SEQ ID NO:19:

(i) SEQUENCE CHARACTERISTICS:
           (A) LENGTH:   7 amino acids
           (B) TYPE:     amino acid
           (C) STRANDEDNESS:  single
           (D) TOPOLOGY:  linear (ii) MOLECULE TYPE:  peptide (xi) SEQUENCE DESCRIPTION:     SEQ ID NO:19:

Leu Gly Ala Gly Gly Ala Gly
1               5

(2) INFORMATION FOR SEQ ID NO:20:

(i) SEQUENCE CHARACTERISTICS:
           (A) LENGTH:   4 amino acids
           (B) TYPE:     amino acid
           (C) STRANDEDNESS:  single
           (D) TOPOLOGY:  linear (ii) MOLECULE TYPE:  peptide
```

(xi) SEQUENCE DESCRIPTION:    SEQ ID NO:20:

Ala Ile Pro Gly
1

(2) INFORMATION FOR SEQ ID NO:21:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:21:

Leu Gly Pro Gly Gly
1               5

(2) INFORMATION FOR SEQ ID NO:22:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:22:

Ala Ala Ala Gln Ala
1               5

(2) INFORMATION FOR SEQ ID NO:23:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:23:

Val Gly Val Xaa Gly
1               5

(2) INFORMATION FOR SEQ ID NO:24:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:    SEQ ID NO:24:

Val Tyr Pro Gly Gly
1               5

(2) INFORMATION FOR SEQ ID NO:25:

(i) SEQUENCE CHARACTERISTICS:
            (A) LENGTH:  6 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:     SEQ ID NO:25:

Ile Gly Gly Val Gly Gly
1               5

(2) INFORMATION FOR SEQ ID NO:26:

(i) SEQUENCE CHARACTERISTICS:
            (A) LENGTH:  6 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:     SEQ ID NO:26:

Val Ala Pro Gly Val Gly
1               5

(2) INFORMATION FOR SEQ ID NO:27:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:     SEQ ID NO:27:

Leu Gly Val Gly Gly
1               5

(2) INFORMATION FOR SEQ ID NO:28:

(i) SEQUENCE CHARACTERISTICS:
            (A) LENGTH:  4 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:     SEQ ID NO:28:

Val Leu Pro Gly
1

(2) INFORMATION FOR SEQ ID NO:29:

(i) SEQUENCE CHARACTERISTICS:
            (A) LENGTH:  5 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:     SEQ ID NO:29:

Phe Arg Ala Ala Ala
1               5

(2) INFORMATION FOR SEQ ID NO:30:

(i) SEQUENCE CHARACTERISTICS:
            (A) LENGTH:  6 amino acids
            (B) TYPE:  amino acid
            (C) STRANDEDNESS:  single
            (D) TOPOLOGY:  linear (ii) MOLECULE TYPE:  peptide (xi) SEQUENCE DESCRIPTION:     SEQ ID NO:30:

Val Gly Gly Val Pro Gly
1               5

(2) INFORMATION FOR SEQ ID NO:31:

(i) SEQUENCE CHARACTERISTICS:
        (A) LENGTH:  5 amino acids
        (B) TYPE:    amino acid
        (C) STRANDEDNESS: single
        (D) TOPOLOGY: linear (ii) MOLECULE TYPE:  peptide (xi) SEQUENCE DESCRIPTION:     SEQ ID NO:31:

Phe Gly Pro Gly Gly
1               5

(2) INFORMATION FOR SEQ ID NO:32:

(i) SEQUENCE CHARACTERISTICS:
        (A) LENGTH:  5 amino acids
        (B) TYPE:    amino acid
        (C) STRANDEDNESS: single
        (D) TOPOLOGY: linear (ii) MOLECULE TYPE:  peptide (xi) SEQUENCE DESCRIPTION:     SEQ ID NO:32:

Val Gly Val Pro Gly
1               5

(2) INFORMATION FOR SEQ ID NO:33:

(i) SEQUENCE CHARACTERISTICS:
        (A) LENGTH:  6 amino acids
        (B) TYPE:    amino acid
        (C) STRANDEDNESS: single
        (D) TOPOLOGY: linear (ii) MOLECULE TYPE:  peptide (xi) SEQUENCE DESCRIPTION:     SEQ ID NO:33:

Val Leu Pro Gly Ala Gly
1               5

(2) INFORMATION FOR SEQ ID NO:34:

(i) SEQUENCE CHARACTERISTICS:
        (A) LENGTH:  5 amino acids
        (B) TYPE:    amino acid
        (C) STRANDEDNESS: single
        (D) TOPOLOGY: linear (ii) MOLECULE TYPE:  peptide (xi) SEQUENCE DESCRIPTION:     SEQ ID NO:34:

Val Gly Leu Xaa Gly
1               5

(2) INFORMATION FOR SEQ ID NO:35:

(i) SEQUENCE CHARACTERISTICS:
        (A) LENGTH:  5 amino acids
        (B) TYPE:    amino acid
        (C) STRANDEDNESS: single
        (D) TOPOLOGY: linear (ii) MOLECULE TYPE:  peptide

```
    (xi) SEQUENCE DESCRIPTION:     SEQ ID NO:35:

Leu Gly Val Gly Ala
1               5

(2) INFORMATION FOR SEQ ID NO:36:

(i) SEQUENCE CHARACTERISTICS:
          (A) LENGTH:  4 amino acids
          (B) TYPE:  amino acid
          (C) STRANDEDNESS:  single
          (D) TOPOLOGY:  linear (ii) MOLECULE TYPE:  peptide (xi) SEQUENCE DESCRIPTION:     SEQ ID NO:36:

Ala Phe Pro Gly
1

(2) INFORMATION FOR SEQ ID NO:37:

(i) SEQUENCE CHARACTERISTICS:
          (A) LENGTH:  5 amino acids
          (B) TYPE:  amino acid
          (C) STRANDEDNESS:  single
          (D) TOPOLOGY:  linear (ii) MOLECULE TYPE:  peptide (xi) SEQUENCE DESCRIPTION:     SEQ ID NO:37:

Ala Phe Pro Gly Ala
1               5

(2) INFORMATION FOR SEQ ID NO:38:

(i) SEQUENCE CHARACTERISTICS:
          (A) LENGTH:  5 amino acids
          (B) TYPE:  amino acid
          (C) STRANDEDNESS:  single
          (D) TOPOLOGY:  linear (ii) MOLECULE TYPE:  peptide (xi) SEQUENCE DESCRIPTION:     SEQ ID NO:38:

Val Gly Ile Pro Ala
1               5

(2) INFORMATION FOR SEQ ID NO:39:

(i) SEQUENCE CHARACTERISTICS:
          (A) LENGTH:  6 amino acids
          (B) TYPE:  amino acid
          (C) STRANDEDNESS:  single
          (D) TOPOLOGY:  linear (ii) MOLECULE TYPE:  peptide (xi) SEQUENCE DESCRIPTION:     SEQ ID NO:39:

Val Gly Gly Ile Pro Thr
1               5

(2) INFORMATION FOR SEQ ID NO:40:

(i) SEQUENCE CHARACTERISTICS:
          (A) LENGTH:  7 amino acids
          (B) TYPE:  amino acid
          (C) STRANDEDNESS:  single
          (D) TOPOLOGY:  linear (ii) MOLECULE TYPE:  peptide
```

```
        (xi) SEQUENCE DESCRIPTION:    SEQ ID NO:40:

Val Gly Val Gly Val Pro Gly
1               5

(2) INFORMATION FOR SEQ ID NO:41:

(i) SEQUENCE CHARACTERISTICS:
         (A) LENGTH:  6 amino acids
         (B) TYPE:    amino acid
         (C) STRANDEDNESS:  single
         (D) TOPOLOGY:      linear (ii) MOLECULE TYPE:  peptide (xi) SEQUENCE DESCRIPTION:    SEQ ID NO:41:

Leu Gly Pro Gly Val Gly
1               5
```